(12) United States Patent
Gaynor-Krupnick

(10) Patent No.: US 12,233,193 B2
(45) Date of Patent: Feb. 25, 2025

(54) URINE COLLECTION DEVICE AND METHOD OF COLLECTING URINE

(71) Applicant: Darlene Michelle Gaynor-Krupnick, Gladwyne, PA (US)

(72) Inventor: Darlene Michelle Gaynor-Krupnick, Gladwyne, PA (US)

( * ) Notice: Subject to any disclaimer, the term of this patent is extended or adjusted under 35 U.S.C. 154(b) by 0 days.

(21) Appl. No.: 18/814,064

(22) Filed: Aug. 23, 2024

(65) Prior Publication Data

US 2024/0416021 A1     Dec. 19, 2024

Related U.S. Application Data

(63) Continuation-in-part of application No. PCT/US2024/016674, filed on Feb. 21, 2024.

(60) Provisional application No. 63/576,648, filed on Feb. 27, 2023.

(51) Int. Cl.
*A61F 5/455*     (2006.01)
*A61F 13/472*    (2006.01)
*A61M 1/00*      (2006.01)
*A61F 5/44*      (2006.01)
*A61F 13/45*     (2006.01)

(52) U.S. Cl.
CPC .............. *A61M 1/71* (2021.05); *A61F 5/455* (2013.01); *A61F 13/472* (2013.01); *A61M 1/84* (2021.05); *A61F 5/4401* (2013.01); *A61F 2013/4506* (2013.01); *A61M 2202/0496* (2013.01)

(58) Field of Classification Search
CPC ........ A61F 5/44; A61F 5/4401; A61F 5/4404; A61F 5/451; A61F 5/455; A61F 2013/15154; A61F 2013/4506; A61M 1/71; A61M 1/84
See application file for complete search history.

(56) References Cited

U.S. PATENT DOCUMENTS

| | | | |
|---|---|---|---|
| 4,747,166 A * | 5/1988 | Kuntz | A61F 5/455 4/144.1 |
| 5,004,463 A | 4/1991 | Nigay | |
| 8,303,554 B2 * | 11/2012 | Tsai | A61B 5/445 604/347 |

(Continued)

OTHER PUBLICATIONS

International Search Report for PCT/US2024/016674, mailed Jun. 3, 2024.
Written Opinion for PCT/US2024/016674, mailed Jun. 3, 2024.

*Primary Examiner* — Catharine L Anderson
(74) *Attorney, Agent, or Firm* — Devlin Law Firm LLC

(57) ABSTRACT

A urine collection system utilizes a pump to draw urine from a urine collection body having an insert portion, configured for optional vaginal insertion and a collection portion configured with a reservoir and reservoir opening to collect urine therein. A body conduit extends within the reservoir of the collection portion and under a top cover portion of the insert portion, or within the insert enclosure formed by the insert portion. The insert portion has apertures to allow urine to be drawn therethrough and into the insert enclosure. A pad or a disposable material may be configured over the reservoir opening of the collection portion and may be permeable to allow urine to pass therethrough. The body conduit may have body conduit apertures from the collection end coupled with a pump conduit, extending to said pump, and the extended end, configured within the insert enclosure.

20 Claims, 16 Drawing Sheets

(56) References Cited

U.S. PATENT DOCUMENTS

2020/0315838 A1   10/2020  Eckert
2021/0000637 A1    1/2021  VanMiddendorp et al.
2021/0170079 A1    6/2021  Radl et al.
2021/0236323 A1    8/2021  Austermann et al.

* cited by examiner

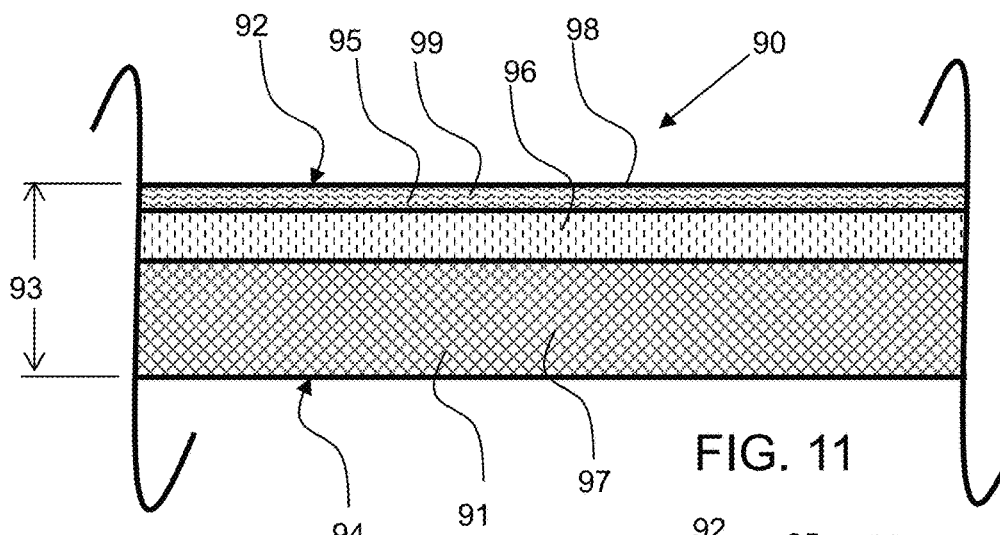
FIG. 11
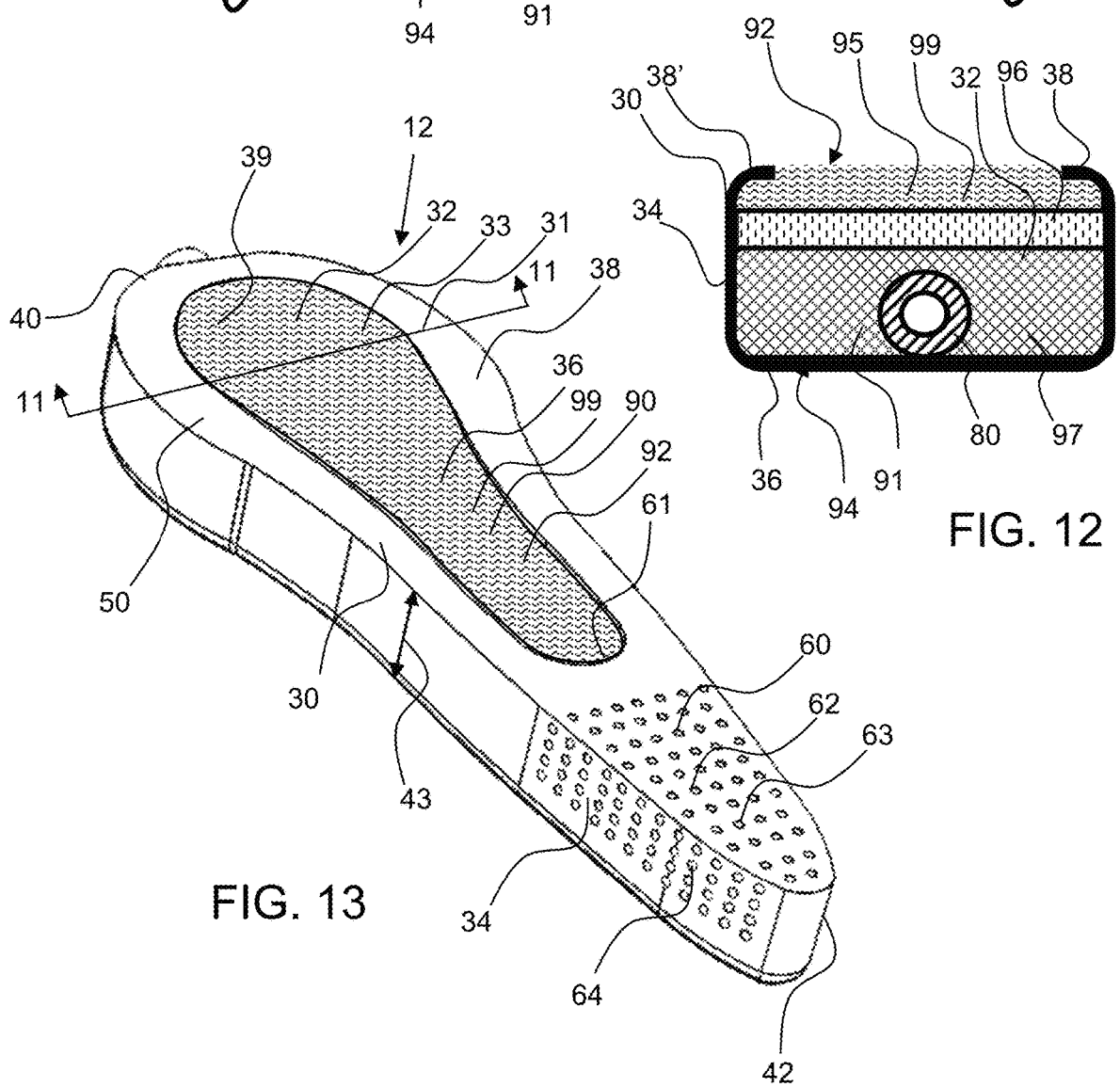
FIG. 12
FIG. 13

URINE COLLECTION DEVICE AND METHOD OF COLLECTING URINE

CROSS REFERENCE TO RELATED APPLICATIONS

This application is a continuation in part of international patent application No. PCT/US2024/016674, filed on Feb. 21, 2024, which claims the benefit of priority to U.S. provisional patent application No. 63/576,648, filed on Feb. 27, 2023; the entirety of which is hereby incorporated by reference herein.

BACKGROUND OF THE INVENTION

Field of the Invention

The invention relates to a urine collection system that utilizes a pump to draw urine from a urine collection body having an insert portion, configured for optional vaginal insertion, and a collection portion configured with a reservoir and reservoir opening to collect urine therein.

Background

For people that are bedridden or injured and cannot make it readily to the bathroom, they may require an incontinence garment or a urine collection device. Current urine collection devices have problems with pooling as suction is only configured from a single orifice or location of a collection body. Also, when the urine collection device is not properly oriented, there may be pooling within the collector, which can lead to leaks. This pooling and exposure to urine over extended period of time may lead to increased risk of urinary tract infections. Furthermore, current active urine collection devices that are coupled with a pump are large and bulky and do not enable mobility when wearing or using the device.

SUMMARY OF THE INVENTION

The invention is directed to a urine collection system that utilizes a pump to draw urine from a urine collection body having an insert portion, configured for optional vaginal insertion, and a collection portion configured with a reservoir and reservoir opening to collect urine therein. A body conduit extends within the reservoir of the collection portion and under a top cover portion of the insert portion, or within the insert enclosure formed by the insert portion. The insert portion has apertures to allow urine to be drawn therethrough and into the insert enclosure. The top cover portion may be detachable to the urine collection body and may extend over a portion of the reservoir opening, such as on the insert end, or over the entire reservoir opening. A pad or a disposable material may be configured over the reservoir opening of the collection portion and may be permeable to allow urine to pass therethrough. The body conduit may have body conduit apertures along a substantial portion of the length of the body conduit, such as at least 75% of a length of the body conduit, at least 85% of a length of the body conduit, at least 95% of a length of the body conduit, and any range between and including the percentages provided. These high percentages may ensure that urine is drawn from reservoir along the full length of the reservoir. The body conduit apertures may be in the body conduit from the pump end of the body conduit, coupled with the pump conduit, and the extended end of the pump conduit, which may be configured in the inert enclosure.

The body conduit apertures may have a size, such as a diameter or maximum cross-opening dimension of about 1 mm or more, about 2 mm or more, about 3 mm or more, about 5 mm or less and any ranges between and including the values provided. A body conduit may have a large number of body conduit apertures, such as about 10 or more, about 20 or more, about 30 or more, about 50 or more, about 100 or more, about 200 or more and any range between and including the number of body conduit apertures listed. Again, a high number of apertures and apertures configured substantially along the length of the body conduit from a pump end to an extended end.

The body conduit may extend in a serpentine configuration wherein the body conduit undulates back and forth along a portion of the length of the urine collection body from the collection end to the extended end to increase the effectiveness of drawing urine therein. The body conduit may coil within the reservoir and insert portion wherein it extends along the length toward the insert end and coils back toward the reservoir end. The body conduit may curve back and forth, undulate or serpentine, or coil within the reservoir such that the body conduit covers a substantial surface area of the reservoir base, or about 70% or more of the surface area, about 80% or more, about 90% or more or any range between and including the values provided. The area of coverage of the body conduit may be calculated by the product of the diameter and length of the body conduit, when the body conduit is a tube having a circular cross-section. Put another way, the length of the body conduit within the reservoir may be greater than the length of the urine collection body from the reservoir end of the insert end, such as about 1.5 times or greater, about 1.75 times or greater, about 3 times or greater, about 5 times or greater, about 10 times or greater and any range between and including the values provided.

The body conduit may extend to, through or into a reservoir tube aperture in the reservoir end of the urine collection body. The pump conduit may extend to, into or through the same reservoir tube aperture and couple with the body conduit to enable the pump to produce a vacuum and draw the urine into first the body conduit and then into the pump conduit for collection. The pump may be a battery operated pump being coupled with a battery, such as a battery in a housing of the pump that supply electrical power to the pump.

The urine collection body may have a shape conducive for effectively collecting urine and also for comfort. The edges of the urine collection body may be curved, such as having rounded edges between the side walls and the reservoir flange and/or the base of the urine collection body. The shape of the urine collection body from the collection portion to the insert portion may taper, wherein the insert portion tapers to the insert end for ease of insertion into an undergarment and optionally vaginal insertion. The collection portion may be bulbous and have curved sides for comfort, wherein the collection portion is configured to extend forward from the insert portion between a woman's legs and along the vulvar arear. The collection portion may have a maximum width that is wider than a width of insert portion taken an offset distance of about 30 mm from the insert end of the urine collection body, such as about 1.25 times or more, about 1.5 times or more, about 2.0 times or more, about 2.5 times or more, about 3 times or more and any range between and including the values provided.

The insert portion forms and insert enclosure with an opening to this insert enclosure along the reservoir. The insert enclosure has a top cover portion, side walls and a base and each of these faces may have apertures to allow urine to flow therethrough. The collection portion has reservoir opening along the top of the collection portion and is configured for a fluid permeable pad or cover to extend thereover. An insert enclosure may be configured on the insert end or insert portion of the urine collection body and may have a top cover portion that extends over the reservoir of the urine collection body and this insert enclosure may have apertures for receiving bodily fluid including urine into the reservoir. The insert enclosure may be formed in part by a detachable top cover portion or body contact insert that has top cover apertures for receiving bodily fluid therethrough into the reservoir. A top cover portion or body contact insert may be extend over the reservoir and have flanges for extending under the reservoir flanges to retain the top cover portion to the urine collection body. The top cover portion or body contact insert may have one or more body channel flanges that extend toward the base of the reservoir to retain the body conduit within the reservoir.

The body conduit extends along the reservoir of the collection portion and into the insert enclosure of the insert portion and has apertures to collect urine along the length of the body conduit. The body conduit may extend in a serpentine configuration, or back and forth from side to opposing side of the reservoir to provide more surface area, or length of body conduit for more effective urine collection.

The urine collection body may be made out of a soft and supple material for comfort, such as a soft plastic or an elastomeric material, such as silicone of polyurethane. An elastomeric material is a material that can be deformed by a deforming force and then return to an original shape upon removal of the deforming force.

A urine collection system may include a urine collector, such as a bag or other container that is coupled with the pump conduit 16 and pump 14 to collect urine therein. A valve may be used to close off the flow of urine to the urine collector. The valve may be closed and the urine collector may be detached and disposed of or may be emptied of urine and then reattached for additional urine collection.

The urine collection body, or a portion thereof, and or the body conduit may include an antimicrobial, antibacterial or antibiotic coating. This coating may prevent bacterial growth and reduce the likelihood of urinary tract infections. An antimicrobial may be silver and it may be added to the mixture of the biocompatible silicone mold or may be included in a coating.

A urine collection system may include a pad that is configured to fit within the reservoir of the urine collection body to prevent urine from contacting the wearer. The pad may be configured and shaped for insertion into the reservoir having an enlarged rounded end and a narrower extension from this enlarged rounded end. The pad may have a plurality of layers that are configured to allow the urine to be drawn through the body conduit and prevent urine from contacting the wearer. A base layer configured along the base of the reservoir or a base side, which may be a foam, a fabric layer configured opposite the base layer and configured along a body contact surface of the pad and a wicking layer configured between the base layer and body contact layer. The top cover portion may be detachably attachable to the urine collection body and extend over the pad, wherein the pad is configured between the base of the reservoir and the top cover portion within the reservoir.

The pad may include a base layer that is relatively thick and configured on the base surface of the pad to extend over and around the body conduit. The base layer of the pad may be configured to prevent urine or other bodily fluids from flowing freely within the reservoir. The base layer may be a foam, such as an open cell foam, that may have a pore size of about 1 mm or more, about 2 mm or more, about 5 mm or more, about 10 mm or more and any range between and including the values provide. The base layer may have a thickness that enables the foam to deform and extend around the body conduit. The foam may be considered a sponge to prevent any liquid from flowing out from the reservoir but may not retain the liquid, so that it can easily be drawn by vacuum into the body conduit for collection. The base layer, such as a foam, may be made from a material that is hydrophobic, such as a polymer including hydrocarbon polymers such as polyethylene, polypropylene or a urethane, silicone and the like.

The pad may include a body contact layer configured on an opposite side of the pad from the base layer and is configured along the body contact surface of the pad. The body contact layer may be a fabric that is comfortable against a person's skin, such as a non-woven or woven fabric. A pad or any portion or layer of the pad may include an antibacterial material, such as a coating, on one or more of the layers.

A pad may include a wicking layer, configured between the base layer and body contact layer and configured to wick any fluid that flows up through the base layer to prevent it from flowing further to the body contact layer. The wicking layer may be configured to wick fluid within the wicking layer, or laterally so that it spread the fluid out over the wicking layer. The wicking layer may be foam or membrane or a natural material such as cotton and may be woven to increase wicking along the fibers of the woven material. Woven material with fibers having a plurality of strands may effectively wick fluids along the fibers laterally to spread out fluid over the surface area of the wicking layer. When the wicking layer is a foam or membrane, the pore size may be much smaller than the average pore size of the base layer, such as about half or less, about a quarter or less, about one-eight or less. The average pore size of the wicking layer may be about 1 mm less, about 500 µm or less, about 100 µm or less, about 50 µm or less and any range between and including the values provide. Again, this smaller average pore size as determined by a coulter porometer, may effectively retain fluid and prevent the fluid from flowing into the body contact layer. A wicking layer may be a layer of cotton that is felted as well. Likewise, the thickness of the wicking layer may be much less than the thickness of the base layer, such as about half or less, about a quarter or less, about one-eight or less.

A pad may be configured for disposal between uses and may be easily detachable from the body of the urine collection body. The pad may extend over the reservoir or over the reservoir opening along the body contact side of the urine collection body. The pad or at least one or more of the layers of the pad may extend into the insert enclosure of the insert portion.

A urine collection system may be portable and configured for use by people that are mobile, such as being in a wheelchair. The urine collection system of the present invention may be useful for those in nursing homes and/or those temporarily injured or disable and bound to a wheelchair. The urine collection system may be used for a person that is mobile and walks with the urine The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 11 shows a side view of an exemplary pad configured to fit within the reservoir of the urine collection body to prevent urine from contacting the wearer.

FIG. 12 shows a cross sectional view along line 11-11 of FIG. 12.

FIG. 13 shows a front-side perspective view of a urine collection device having an insert portion and collection portion and a pad configured in the reservoir to prevent urine from contacting the wearer.

Figure 1:
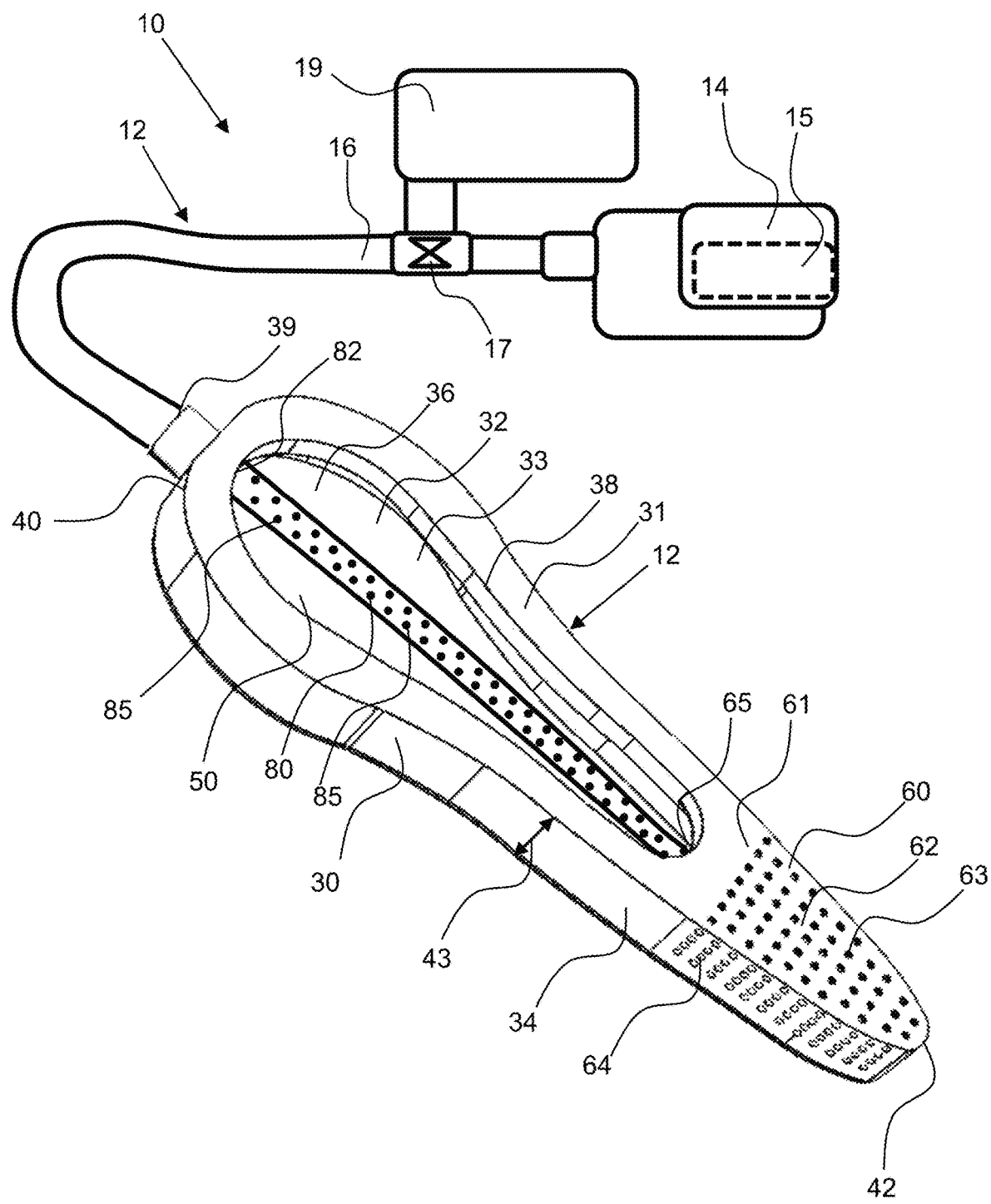
FIG. 1 shows a side perspective view of a urine collection system having a pump coupled to the urine collection body by a pump conduit and a body conduit extending within the reservoir of the urine collection body with apertures to collect urine from along the length of the reservoir.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purpose of illustrating the present invention and should not be interpreted as limiting the scope of the invention. Other embodiments of the invention, and certain modifications, combinations, and improvements of the described embodiments, will occur to those skilled in the art and all such alternate embodiments, combinations, modifications, improvements are within the scope of the present invention.

Referring to FIGS. 1 to 8, a urine collection system 10 has a pump 14 that may be a portable pump being powered by a battery 15. The pump 14 is configured to couple to the urine collection body 30, by a pump conduit 16 and a body conduit 80 extending within the reservoir 32 of the urine collection body with body conduit apertures 85 to collect urine from along the length of the reservoir. The urine collection body has a reservoir opening 33 along the body contact side 31 of the urine collection body 30 to enable urine to pass into reservoir 32. Also a reservoir flange 38 extends along the body contact side 31 from the side walls 34 over a portion of the reservoir 32 to prevent spilling of urine from the urine collection body.

The urine collection body 30 has an insert portion 60 configured for optional vaginal insertion and a collection portion 50 configured to extend forward along the vulva during use. The urine collection body may lay against or within the vaginal labia and buttock and may be secured in place by an undergarment. The urine collection body 30 may be configured to bend or flex and may be made out of a resilient material, as described herein. The urine collection body 30 may have curved our rounded edges between the side wall 34 and the reservoir flange 38 or top surface of the urine collection body 30 and also between the side wall and the base 36 of the urine collection body. The edges may extend at a radius of curvature of at least about 2 mm or more, about 4 mm or more, about 6 mm or more, about 10 mm or more and any range between the values provided. The insert portion 60 has a top cover portion 62 to form an insert enclosure 61 around the reservoir 32 having an insert enclosure opening 65 along the reservoir 32 and wherein the body conduit is configured to extend into this insert enclosure 61 to collect urine from the insert portion 60. This insert enclosure 61 prevents direct contact of the body conduit 80 from touching the interior walls of the vagina. The insert portion has top cover apertures 63, side wall apertures 64 and base apertures 66 configured to allow urine to flow therethrough for collection. The collection portion has a reservoir opening 33 to allow urine to flow directly into the reservoir, or through a pad configured thereover.

As shown in FIG. 1, the body conduit 80 is a tube with a plurality of body conduit apertures 85 configured along the length of the body conduit, from the collection end coupled to the urine collection body 30. The extended end of the body conduit extends within the insert enclosure 61 of the insert portion 60. The body conduit may be detachable from the urine collection body 30 and the pump conduit may also be detachably attachable to the collection body, and also the pump, to allow for cleaning or for replacement. Also, the insert portion is tapered in width from the collection portion. A urine collector 19, such as a bag or other container is coupled with the pump conduit 16 and pump 14 to collect urine therein. A valve 17 may be used to close off the flow of urine to the urine collector.

Figure 2:
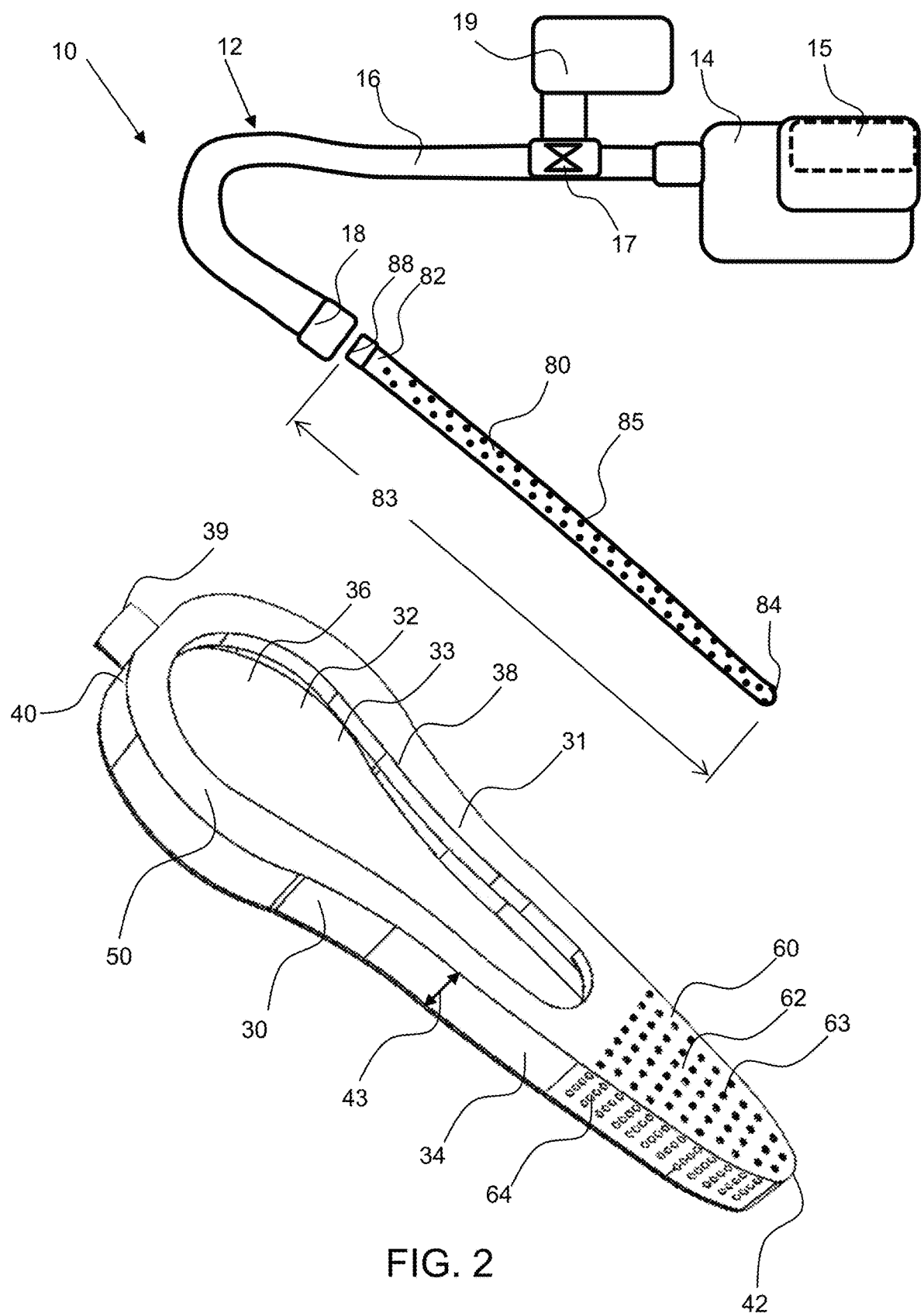
FIG. 2 shows a side perspective view of a urine collection device having an urine collection body detached from the body conduit and pump conduit.

As shown in FIG. 2, the urine collection body 30 is detached from the body conduit 80 and the pump conduit 16 as well as the pump 14. As shown, the body conduit 80 extends a length 83 from a pump end 82 to an extended end 84 that may be closed or sealed to enable a higher vacuum suction through the body conduit apertures 85. The extended end may be configured with the insert portion 60 during use. A body conduit coupler 88 may be configured on the pump end 82 of the body conduit 80 and may be configured to detachably attach to the urine collection body 30, to enable flow through the reservoir tube aperture 39. Also, the pump conduit 16 has a pump conduit coupler 18 configured to detachably attach to the urine collection body 30, to enable flow through the reservoir tube aperture 39. The body conduit 30 being detachably attachable may enable detachment for replacement or cleaning.

Figure 3:
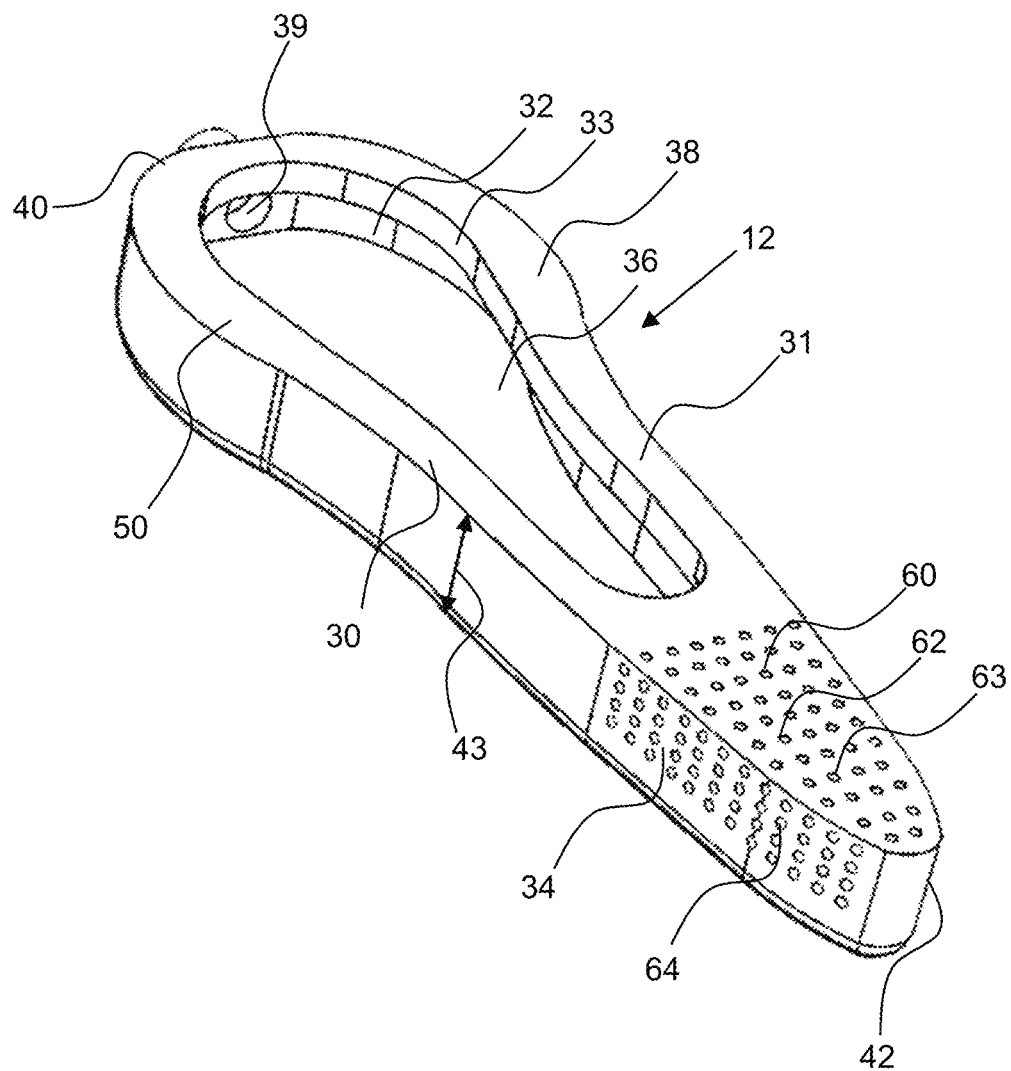
FIG. 3 shows a front-side perspective view of a urine collection body having an insert portion and collection portion.

Referring now to FIGS. 2 and 3, the urine collection device 12 includes a urine collection body 30, a pump 14, a pump conduit 16 and a body conduit configured to extend within the reservoir 32 of the urine collection body. The urine collection body 30 has a collection portion 50 and an insert portion 60. The reservoir 32 is formed by the side walls 34 extending up from the base 36. The collection body has a height 43 that is effective to enable adequate urine collection. The reservoir end 40 of the urine collection body 30 has a reservoir tube aperture 39 to allow urine to flow through the collection body and into the pump conduit.

Figure 4:
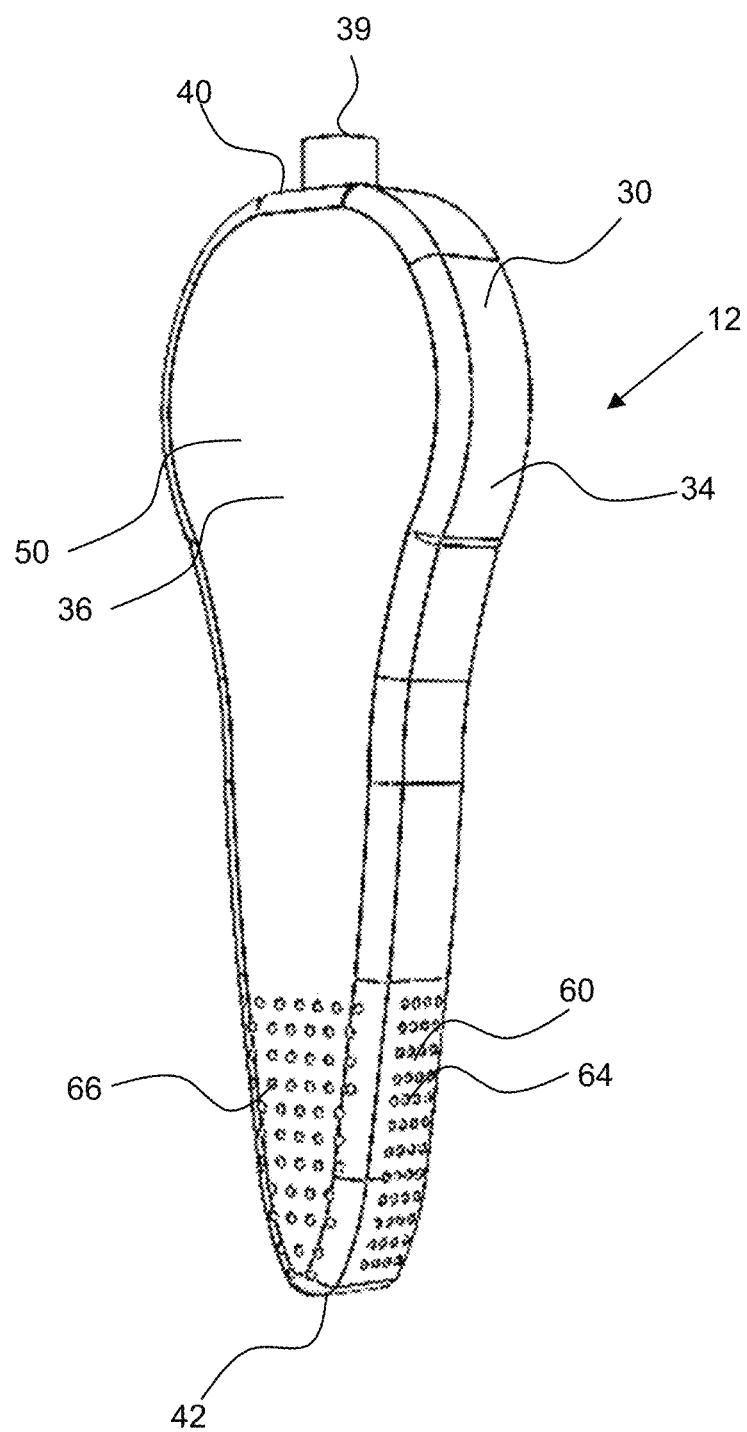
FIG. 4 shows a bottom perspective view of a urine collection body having an insert portion and collection portion.

As shown in FIG. 4, the insert portion 60 has base apertures 66 in the base 36 of the urine collection body 30 along the insert portion 60. Note that the base apertures 66 are not in the collection portion 50, only in the insert portion 60.

Figure 5:
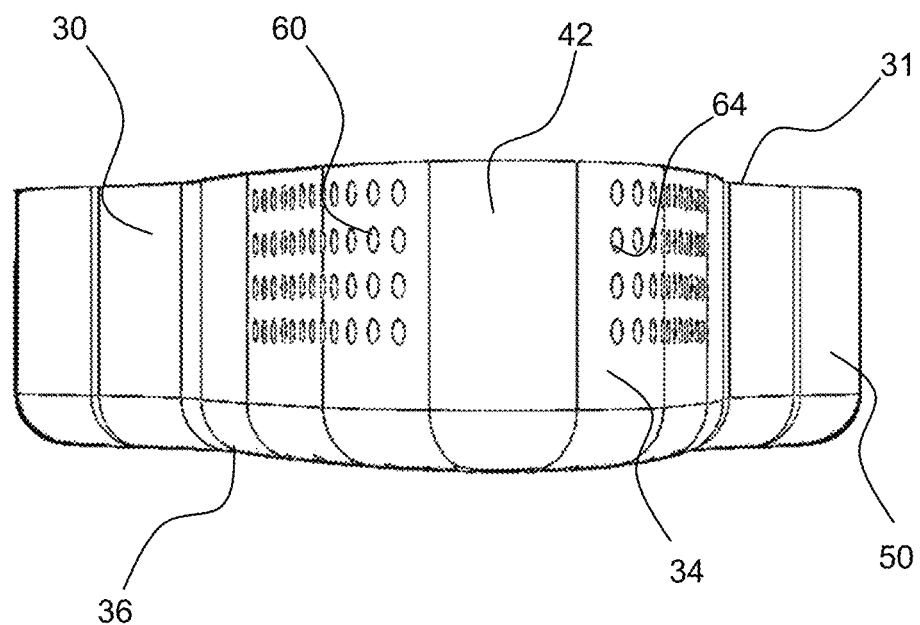
FIG. 5 shows a front view of a urine collection body having an insert portion and collection portion.

As shown in FIG. 5, the insert end 42 of the urine collection body 30 does not have any apertures as this is the most extended portion configured for optional insertion into the vagina. Also, the insert end 42 is curved or rounded for comfort and the surface of the insert end may extend along a radius of curvature of about 5 mm or more, about 10 mm or more, about 20 mm or more, about 30 mm or more and any range between and including the values provided.

Figure 6:
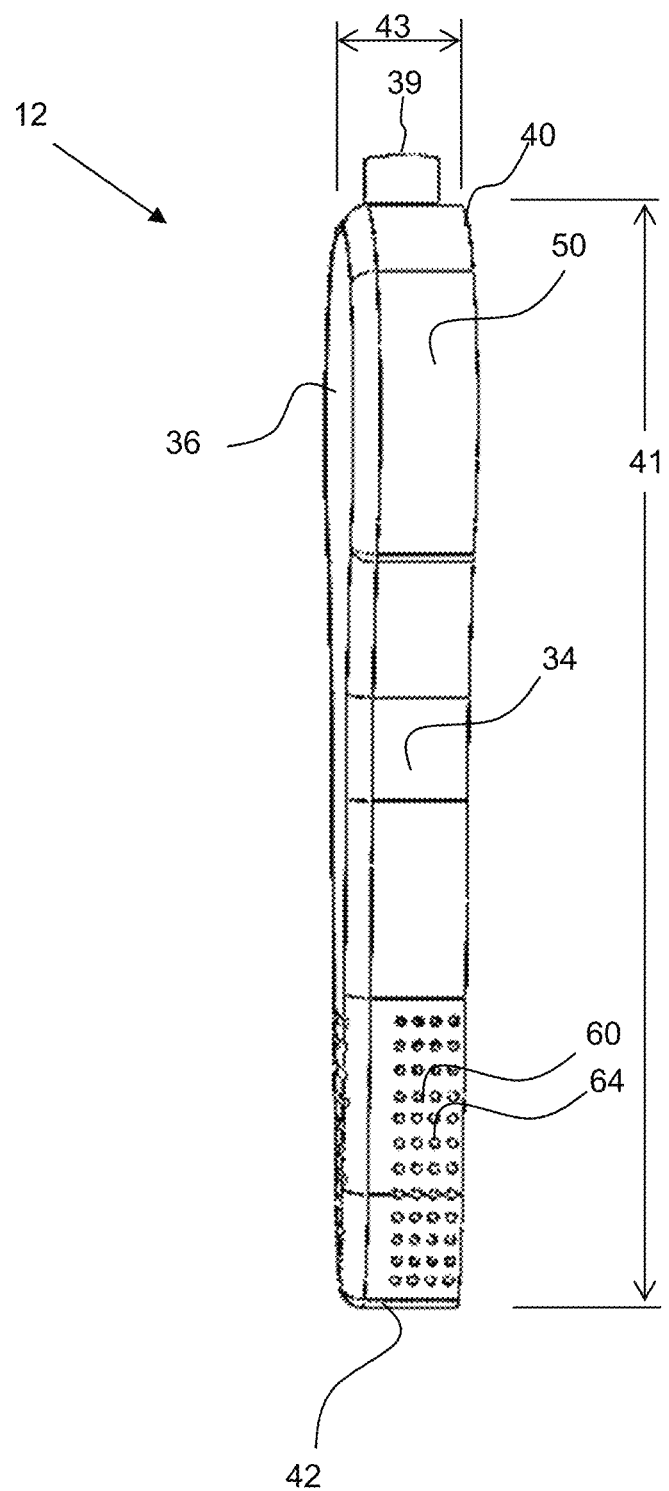
FIG. 6 shows a side-back perspective view of a urine collection body having an insert portion and collection portion.
Figure 7:
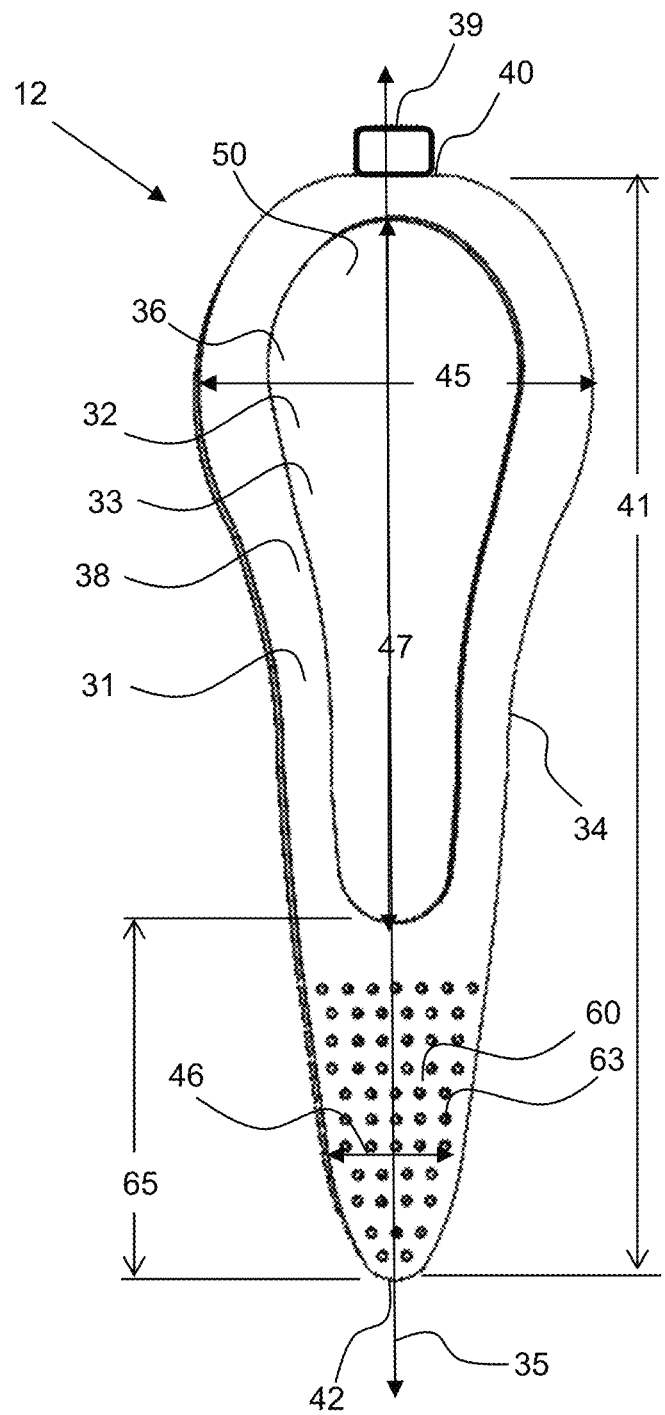
FIG. 7 shows a top view of a urine collection body having an insert portion and collection portion.

Referring now to FIGS. 6 and 7, a urine collection device 12 has a urine collection body 30, with an insert portion 60 extending from the insert end 42 and a collection portion 50 extending from the insert portion 60 to the reservoir end 40. As described herein, the insert portion 60 may taper in width from the collection portion to the insert end 42. As shown the maximum width 45 of the collection portion 50 and collection body is more than double the width 46 of the insert portion 60 taken orthogonal to the length axis 35 of the urine collection body 30 mm from the insert end 42. The length axis extends along the centerline of the urine collection body 30 from the reservoir end 40 to the insert end 42. The length 47 of the collection portion 50 extends from the reservoir end 40 to the insert portion 60 or to the beginning of the insert enclosure 61 as shown. Again, this tapering enables ease of optional vaginal insertion and an effectively wide collection area to extend along the vulvar area. The length 41 of the urine collection body may be about 100 mm or more, about 125 mm or more, about 150 mm or more, about 175 mm or more and any range between and including the values provided. The width 45 of the collection portion 50 may be about 25 mm or more, about 35 mm or more, about 50 mm or more, about 75 mm or more, about 100 mm or more, about 125 mm or more, and any range between and including the width values provided. The width 46 of the insert portion, taken at 30 mm from the insert end 42 may be about 20 mm or more, about 30 mm or more, about 40 mm or more, about 50 mm or more, about 60 mm or more and any range between and including the width values provided.

Figure 8:
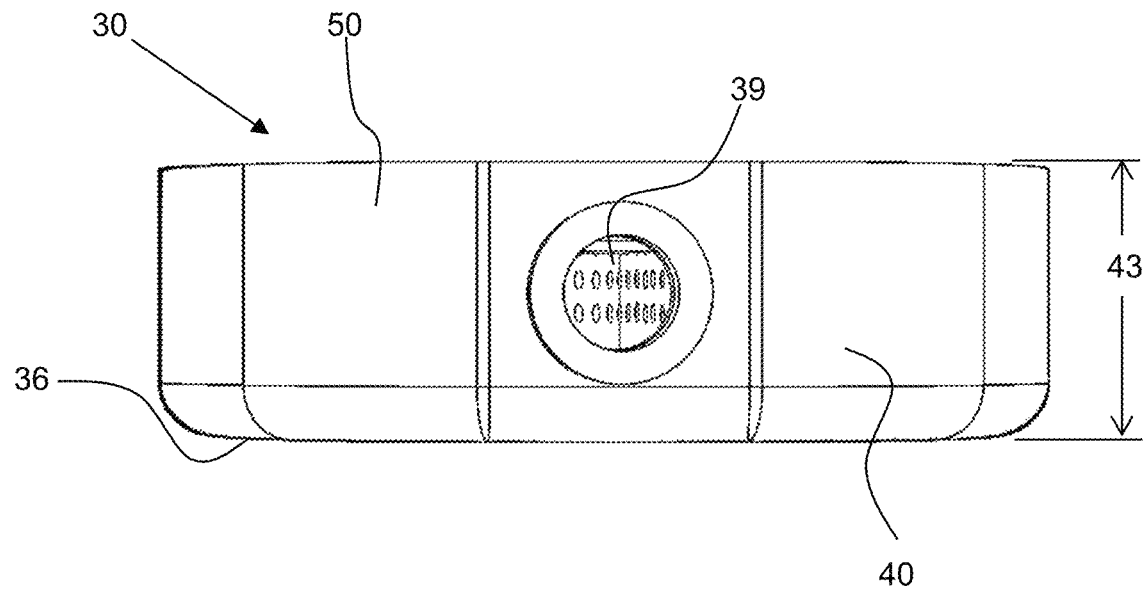
FIG. 8 shows a back view of a urine collection body having an insert portion and collection portion.

FIG. 8 shows the reservoir tube aperture 39 in the collection portion 50 of the urine collection body 30. As described, the pump conduit 16 and the body conduit 80 may be detachable from the tube aperture for replacement and/or for cleaning.

Figure 9:
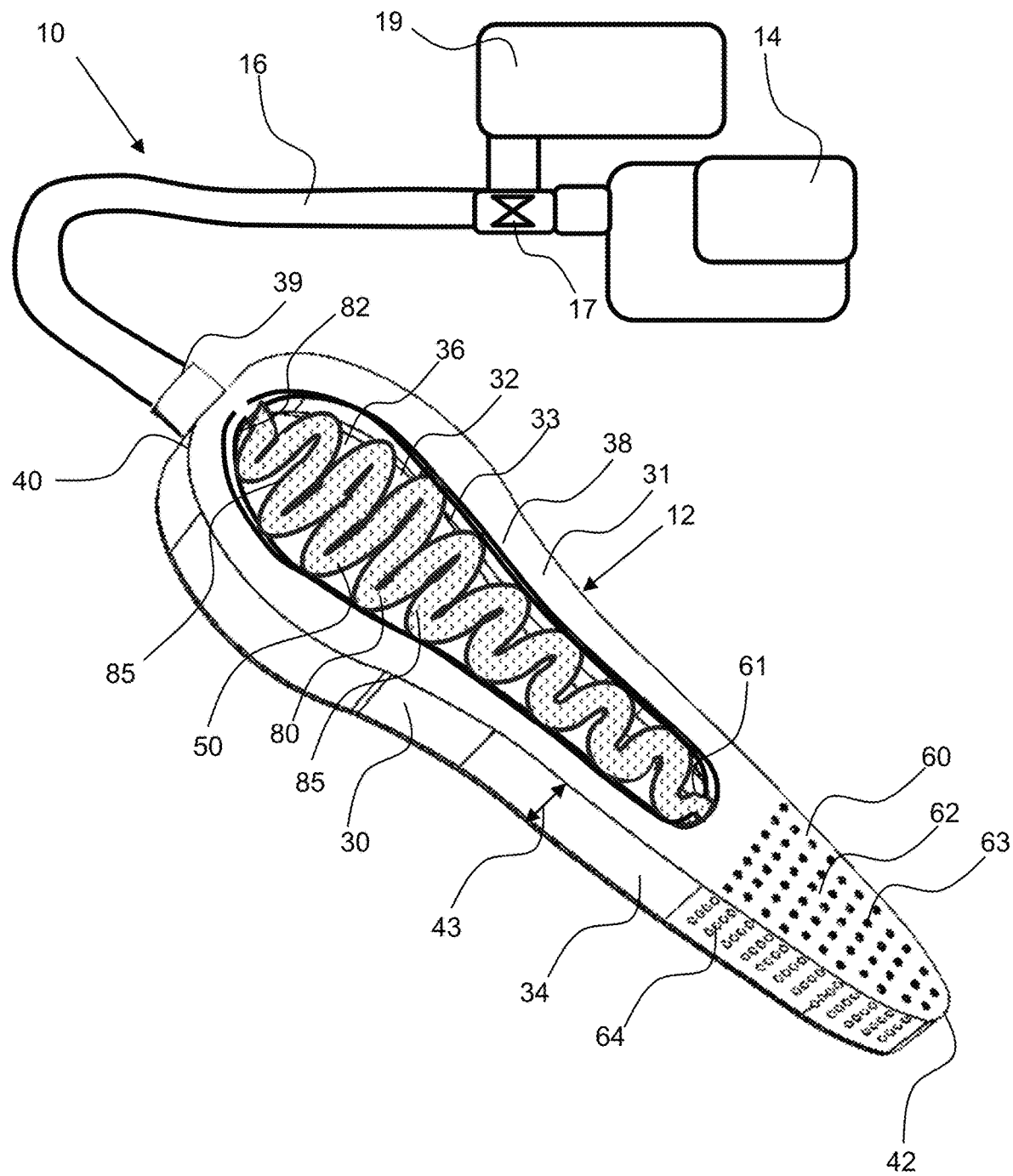
FIG. 9 shows a front-side perspective view of a urine collection body having body conduit that undulates or serpentines back and forth within the reservoir to substantially cover the area of the base of the reservoir.

FIG. 9 shows the body conduit 80 that undulates or serpentines back and forth within the reservoir 32 to substantially cover the area of the base of the urine collection base, or exposed base within the reservoir. The body conduit 80 undulates back and forth within the reservoir 32 such that the body conduit covers a substantial surface area of the base 36 exposed in the reservoir, such as about 70% or more of the surface area of the base of the reservoir as shown. The body conduit 80 is a tube with a plurality of body conduit apertures 85 configured along the length of the body conduit, from the collection end coupled to the urine collection body 30. The extended end of the body conduit extends within the insert enclosure 61 of the insert portion 60. The body conduit may be detachable from the urine collection body 30 and the pump conduit may also be detachably attachable to the collection body, and also the pump, to allow for cleaning or for replacement. Also, the insert portion is tapered in width from the collection portion.

Figure 10:
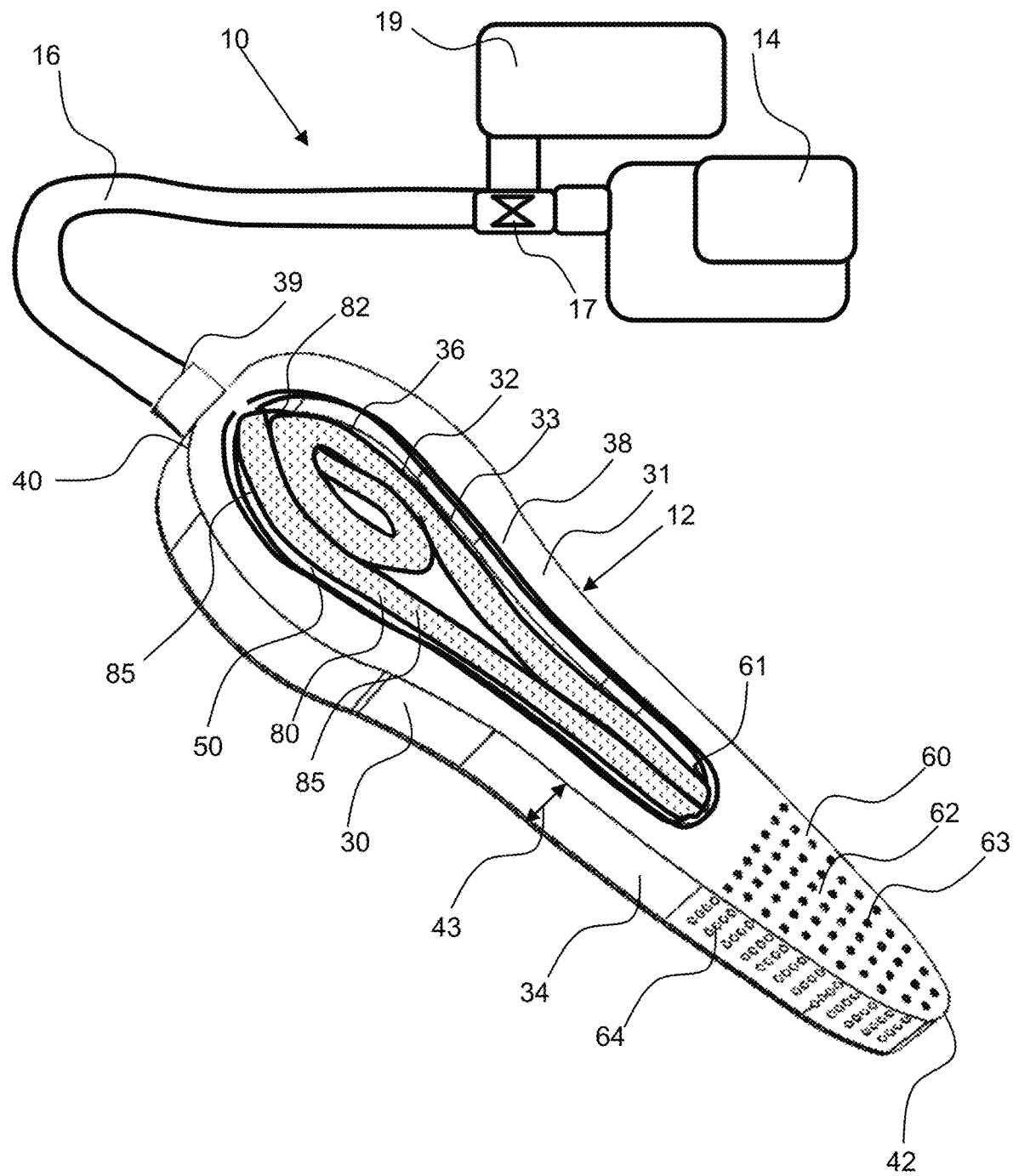
FIG. 10 shows a front-side perspective view of a urine collection body having body conduit that coiled within the reservoir, extending from the reservoir end into the insert portion and then coiling back toward the reservoir end to substantially cover the area of the base of the reservoir.
Figure 14:
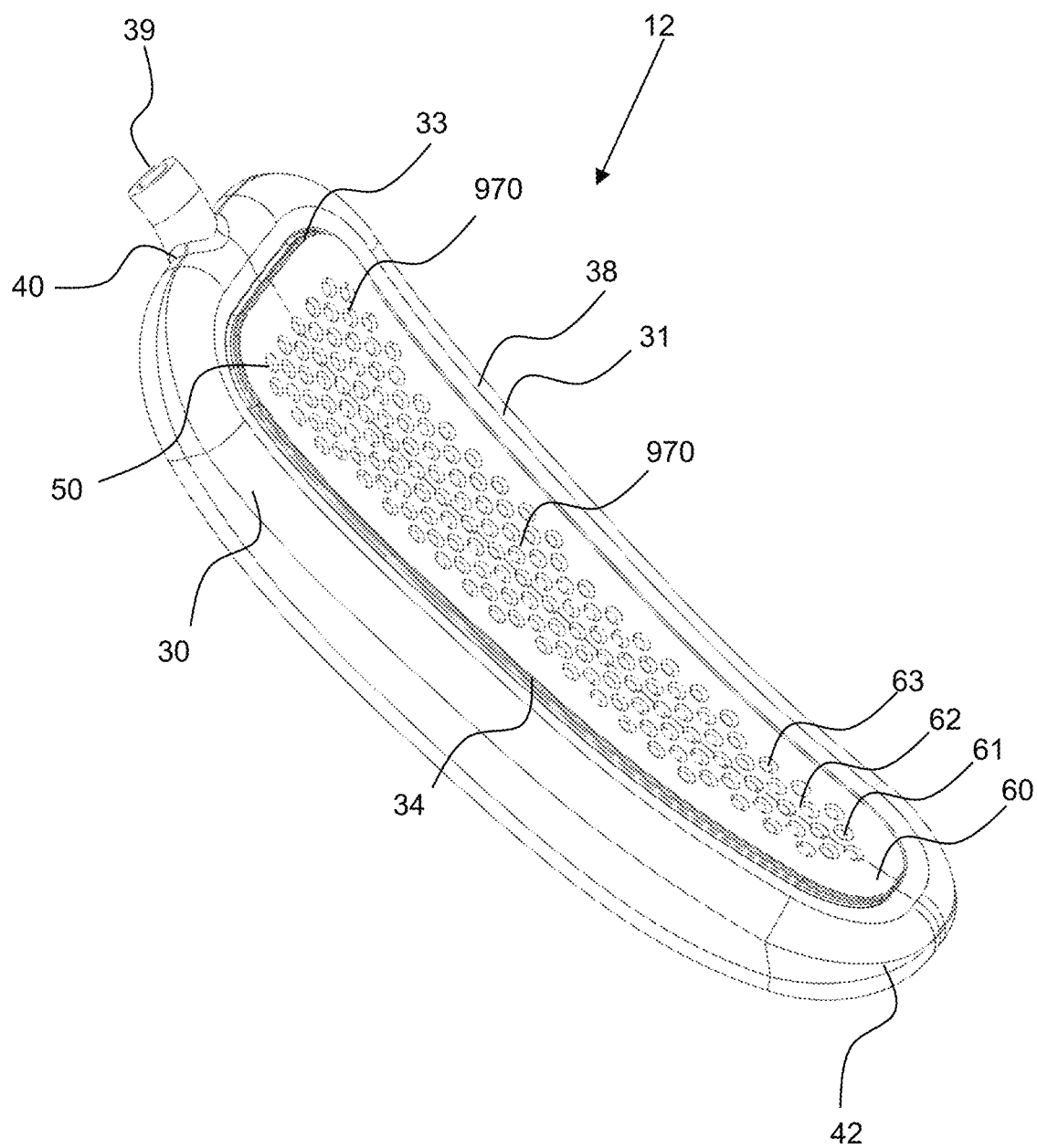
FIG. 14 shows a perspective view of a urine collection device having a top cover portion that extends over the reservoir opening and has apertures for the flow of bodily fluid into the reservoir.

FIG. 10 shows the body conduit 80 that coils within the reservoir 32 to substantially cover the area of the base of the urine collection base, or exposed base within the reservoir. The body conduit 80 coils wherein it extends from the reservoir end 40 toward the insert end 42, into the insert enclosure 61 and then coils back toward the reservoir end to form a coil. As shown the body conduit 80 coils within the reservoir in the collection portion 50, wherein the body conduit coils or folds around itself in the collection portion.

The coiled body conduit in the reservoir 32 covers a substantial surface area of the base 36 exposed in the reservoir, such as about 70% or more of the surface area of the base of the reservoir as shown. The body conduit 80 is a tube with a plurality of body conduit apertures 85 configured along the length of the body conduit, from the collection end coupled to the urine collection body 30. The extended end of the body conduit extends within the insert enclosure 61 of the insert portion 60.

Referring now to FIGS. 11 and 13, an exemplary pad 90 is configured to fit within the reservoir 32 of the urine collection body 30 to prevent urine from contacting the wearer. The pad 90 is configured and shaped for insertion into the reservoir having an enlarged rounded end and a narrower extension from this enlarged rounded end. The pad may be configured to extend up into the insert enclosure 61 of the insert portion 60 to aid in retaining the pad in place. Also, the pad may be held in place by the reservoir flange 38 that extends out over the reservoir 32 from the side wall 34 of the body. An exemplary pad 90 has three layers, a base layer 91 configured to extend along the base surface 94, or along the base of the reservoir and around the body conduit, a body contact layer 99 configured along a body contact surface 92 of the pad and configured for exposure to a person's body or skin, and a wicking layer 96 configured between the base layer 91 and body contact layer 99. An antibacterial material 98 may be configured on the pad 90, such as on the body contact layer 99 to prevent infections. Having the antibacterial proximal to the body contact surface may be preferred to prevent infections due to contact with the body.

The base layer 91 may be foam 97 that prevents urine from freely flowing or sloshing within the reservoir. The body contact layer 99 may be a fabric, such as a woven or non-woven that provides comfort along the body or skin. The wicking layer 96 may be a woven fabric or a foam having a tighter structure or much smaller average pore size than the base layer to prevent fluid from reaching the body contact layer.

The pad 90 may be configured to enable urine to be drawn into the body conduit through apertures in the body conduit and the average pore size of the layers of the pad, and/or the type of materials of the layers may be different for this purpose. The base layer 91 may be a foam 97, such as an open cell foam with a relatively large average pore size to prevent retainment of urine in the base layer. The wicking layer 96 may have a much tighter or smaller pore size than the base layer 91 and may be a much thinner than the foam layer, as described herein. The wicking layer 96 may wick up any urine that may pass through the base layer 91 and retain the fluid such that it does not further wick and pass through to the body contact layer 99. The body contact layer 99, may be a fabric 95 that is a fabric made of a polymer or coated to make the fabric hydrophobic, such that the urine does not wet the fabric. The thickness 93 of the pad is shown and the exemplary relative thicknesses of each layer is shown. The body contact layer 99 is on the body contact surface 92 of the pad 90, opposite the base layer 91. As shown, the thickness of the base layer 91 is much greater than the thickness of the wicking layer 96 and/or the body contact layer 99.

As shown in FIG. 12, the body conduit 80 has the base layer 91 of the pad 90 conforming around the body conduit. The base layer 91 may be a foam layer of foam 97 that has a low durometer and can easily deform around the body conduit within the reservoir 32 of the urine collection body 30.

As shown in FIG. 13, the pad 90 is configured in the reservoir 32, under the reservoir flange 38 and within the insert enclosure 61 of the insert portion 60 to aid in retaining the pad in place to prevent urine from contacting the wearer.

Figure 15:
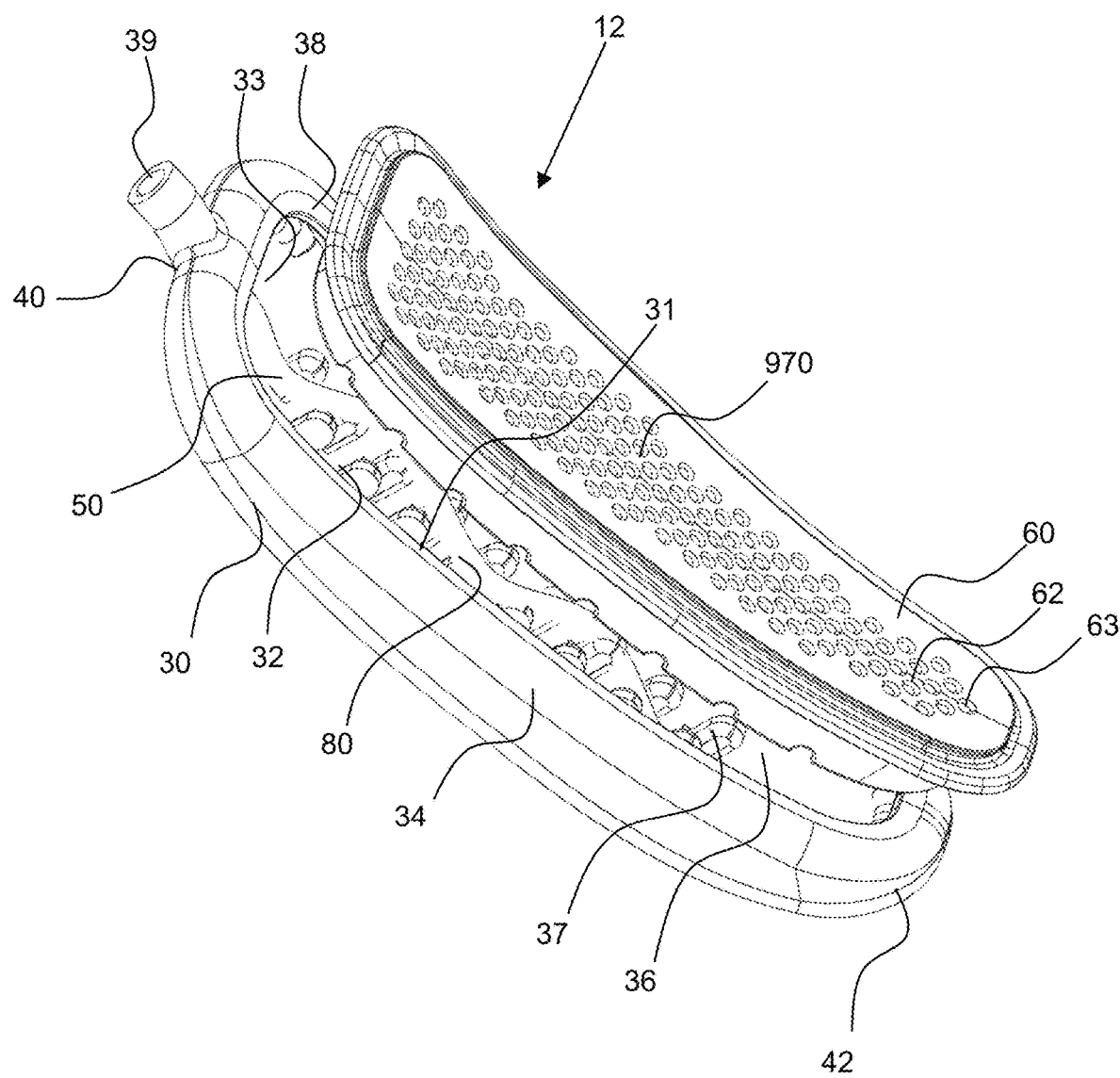
FIG. 15 shows a perspective view of a urine collection device shown in FIG. 14 with the top cover portion, detached from the reservoir and the body conduit extending between reservoir conduit flanges, that extend from the base of the urine collection body.
Figure 16:
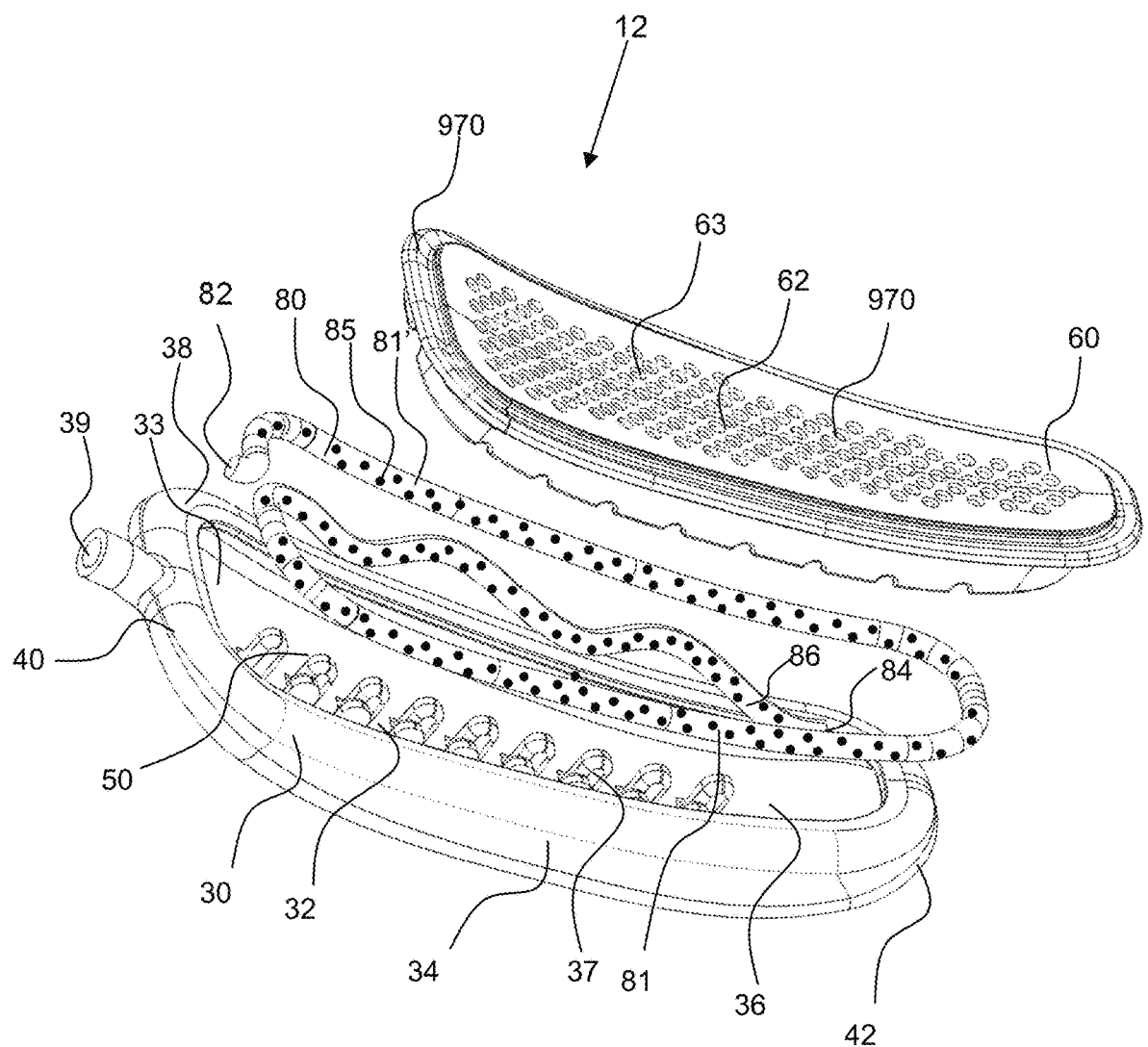
FIG. 16 shows a perspective view of a urine collection device shown in FIG. 14 with the top cover portion, and the body conduit detached from the reservoir.
Figure 17:
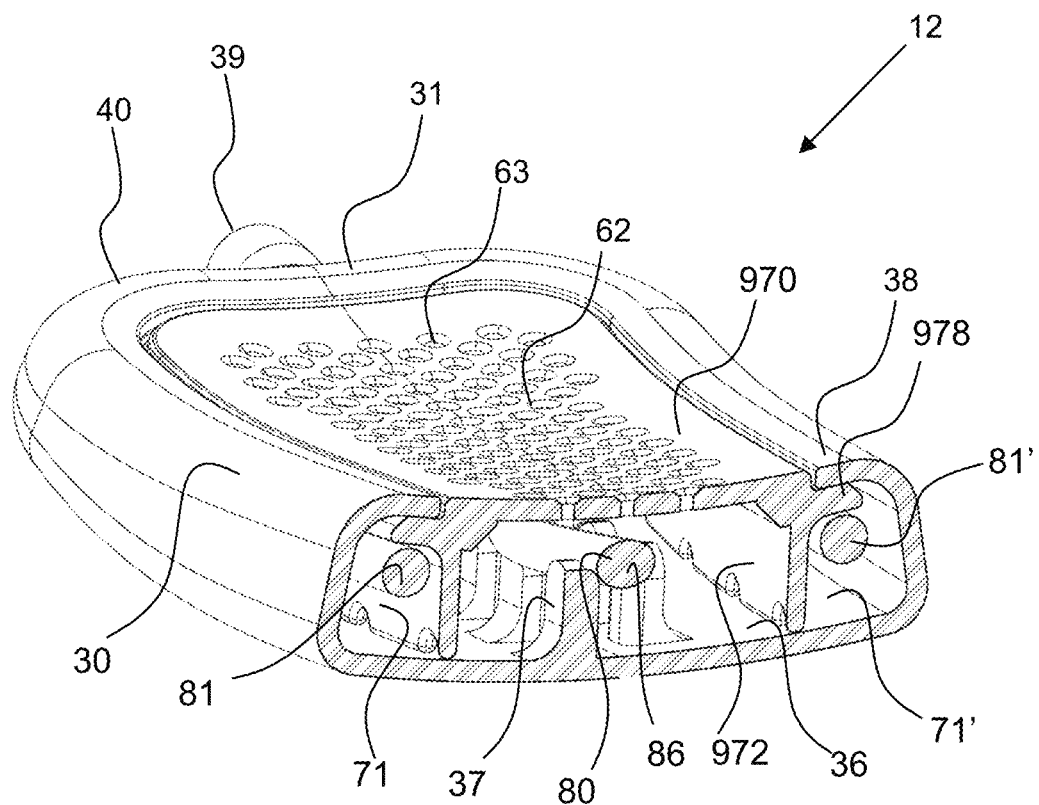
FIG. 17 shows a cross-sectional view across the urine collection device with the top cover portion, coupled to the urine collection body via a body contact flange under the reservoir flange.

Referring now to FIGS. 14 to 18, a urine collection device 12 has a top cover portion 62, having apertures 63 for the flow of bodily fluid into the reservoir 32. The top cover portion 62 extends over the insert portion 60 to form the insert enclosure 61 on the insert end 42 of the urine collection body. The top cover portion 62 may be detachably attachable into the reservoir opening of the urine collection body as shown in FIGS. 15 to 17.

As shown in FIG. 15 and FIG. 16, the urine collection body 30 has reservoir conduit flanges 37 that extend up from the base 36 to retain the body conduit 80 in a fixed position along the reservoir 32 of the urine collection body 30. In FIG. 16, the body conduit 80 is detached from the urine collection body and has outside conduit extensions 81, 81' and a central conduit extension 86. The body conduit extends contiguously from the pump end 82 to the extended end 84. The body conduit 80 has body conduit apertures 85 therethrough to allow bodily fluid to flow therethrough.

Figure 18:
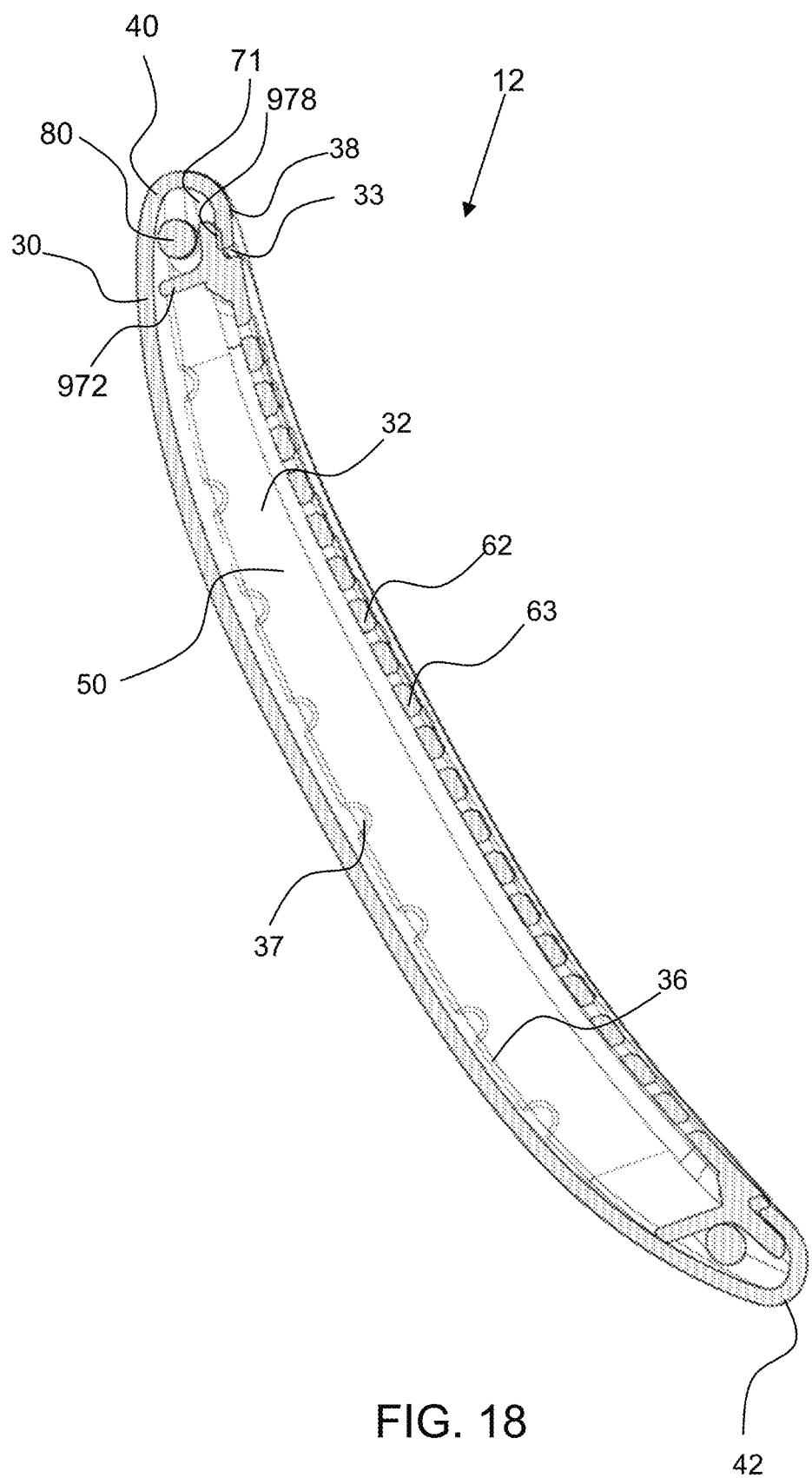
FIG. 18 shows a cross-sectional view along the urine collection device with the body contact layer coupled to the urine collection body and reservoir conduit flanges extending up from the base.

Referring now to FIGS. 16 to 18, the top cover portion 62 forms a body contact insert 970 that is detachably attachable over the reservoir opening 33 and has a body contact flange 978 that extends under the reservoir flange 38 to retain the body contact insert 970 over the reservoir opening 33. The body conduit 80 extends with the outside channel 71, 71' and also within the central channel 76, wherein the channels are formed by the body channel flanges 972 that extend down from the body contact insert 970 toward the base 36 of the urine collection body 30. These channels ensure that the body conduit 80 extends or is configured across the reservoir base to enable rapid removal of bodily fluid from within the reservoir through the body conduit. If the body conduit only extended along the center of the reservoir, bodily fluid may collect along the side of the reservoir and vice versa.

It will be apparent to those skilled in the art that various modifications, combinations, and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A urine collection system comprising:
   a) a pump;
   b) a pump conduit coupled to the pump;
   c) a urine collection body extending from a collection end to an insert end and having a body contact side configured for placement along a woman's body during use, said urine collection body comprising:
      i) collection portion configured on said collection end and comprising:
         a reservoir opening along said body contact side of the urine collection body;
      ii) an insert portion on the insert end, said insert portion comprising:
         an insert enclosure having a plurality of apertures therethrough configured to allow a flow of urine therethrough; and
      iii) a reservoir extending from the collection portion into the insert enclosure of the insert portion;

iv) reservoir tube aperture configured through the collection portion of the urine collection body on the collection end;

d) a body conduit configured in the reservoir;

wherein the body conduit is coupled with the pump conduit and extends into the insert enclosure, said body conduit having body conduit apertures configured to allow urine to flow therethrough;

wherein the pump conduit is fluidly coupled with the body conduit and extends to the pump.

2. The urine collection system of claim 1, wherein the urine collection body is made of an elastomeric material.

3. The urine collection system of claim 1, wherein the urine collection body is a one-piece unit.

4. The urine collection system of claim 1, wherein the body conduit apertures are configured along at least 75% of a length of the body conduit.

5. The urine collection system of claim 1, wherein the body conduit comprises 10 or more body conduit apertures.

6. The urine collection system of claim 1, wherein the insert portion has a top cover portion that extends along the body contact side of the urine collection body and top cover apertures through the top cover portion configured to allow a flow of urine therethrough.

7. The urine collection system of claim 6, wherein the top cover portion is a body contact insert that is detachably attached over the reservoir opening of the urine collection body.

8. The urine collection system of claim 7, wherein the body contact insert comprises a body channel flange that extends toward the base of the urine collection body to retain the body conduit in a channel.

9. The urine collection system of claim 7, wherein the body contact insert has two body channel flanges that extend toward the base of the urine collection body to form two opposing outside channels and a central channel configured between the two opposing outside channels to retain the body conduit along said two opposing outside channel and said central channel.

10. The urine collection system of claim 9, wherein the urine collection body has reservoir conduit flanges that retain the body conduit in position within the reservoir.

11. The urine collection system of claim 1, wherein the urine collection body has reservoir conduit flanges that retain the body conduit in position within the reservoir.

12. The urine collection system of claim 11, wherein the insert portion has a pair of opposing side walls extending from a top cover portion, each having side wall apertures configured to allow a flow of urine therethrough.

13. The urine collection system of claim 1, wherein the insert portion has a pair of opposing side walls extending from a top cover portion, each having side wall apertures configured to allow a flow of urine therethrough.

14. The urine collection system of claim 1, wherein the collection portion has a reservoir flange extending over the reservoir along the collection portion.

15. The urine collection system of claim 14, wherein the insert portion has a top cover portion that extends along the body contact side of the urine collection body and top cover apertures through the top cover portion configured to allow a flow of urine therethrough;

wherein the top cover portion is a body contact insert that is detachably attached over the reservoir opening of the urine collection body and further comprises a body contact flange that engages with the reservoir flange to detachably attach the body contact insert to the urine collection body.

16. The urine collection system of claim 1, wherein the pump is a vacuum pump.

17. The urine collection system of claim 1, wherein the body conduit serpentines along at least a portion of the length of the body conduit from collection end to the extended end.

18. The urine collection system of claim 17, wherein the body conduit has a length that is at least two times greater than a length of the urine collection body.

19. The urine collection system of claim 1, further comprising a pad configured for insertion into the reservoir of the urine collection body.

20. The urine collection system of claim 19, wherein the pad comprises:

a) a base layer configured to extend along a base of the reservoir; and b) a body contact layer configured to extend on a body contact surface of the pad and over the reservoir opening.

* * * * *